(12) United States Patent
Kennis et al.

(10) Patent No.: US 6,303,614 B1
(45) Date of Patent: Oct. 16, 2001

(54) TETRAHYDRO GAMMA-CARBOLINES

(76) Inventors: Ludo Edmond Josephine Kennis; Josephus Carolus Mertens, both of Janssen Pharmaceutica N.V., Turnhoutseweg 30 Beerse (BE), B-2340

( * ) Notice: Subject to any disclaimer, the term of this patent is extended or adjusted under 35 U.S.C. 154(b) by 0 days.

(21) Appl. No.: 09/508,240

(22) PCT Filed: Sep. 1, 1998

(86) PCT No.: PCT/EP98/05710
§ 371 Date: Mar. 7, 2000
§ 102(e) Date: Mar. 7, 2000

(87) PCT Pub. No.: WO99/12926
PCT Pub. Date: Mar. 18, 1999

(30) Foreign Application Priority Data

Sep. 8, 1997 (EP) .................................................. 97202761

(51) Int. Cl.[7] ..................... C07D 471/04; C07D 519/00; A61K 31/435
(52) U.S. Cl. .......................... 514/258; 514/259; 544/282; 544/278; 544/284
(58) Field of Search .................................... 544/282, 278, 544/284; 514/258, 259

(56) References Cited

U.S. PATENT DOCUMENTS 4,798,896   1/1989   Abou-Gharbia et al. .............. 546/87

FOREIGN PATENT DOCUMENTS 0 705 832 A1   4/1996   (EP) .
2180 535       4/1987   (GB) .

Primary Examiner—Mukund J. Shah
Assistant Examiner—Hong Liu
(74) Attorney, Agent, or Firm—Mary Appollina

(57) ABSTRACT

The present invention concerns the compounds of formula

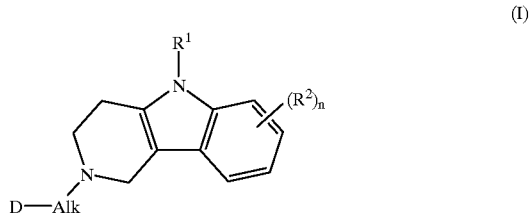

(I)

the N-oxide forms, the pharmaceutically acceptable addition salts and the stereochemically isomeric forms thereof, wherein $R^1$ is hydrogen, optionally substituted $C_{1-6}$alkyl, aryl; $R^2$ is each independently a halogen, hydroxy, $C_{1-6}$alkyl, $C_{1-6}$alkyloxy or nitro; n is 0, 1, 2 or 3; Alk is $C_{1-6}$alkanediyl; D is an optionally substituted saturated or unsaturated nitrogen containing heterocycle; and aryl is optionally substituted phenyl; having a great therapeutic breadth. It further relates to their use as a medicine, their preparation as well as compositions containing them.

11 Claims, No Drawings

TETRAHYDRO GAMMA-CARBOLINES

Cross Reference to Related Applications

This application is a National Stage application under 35 U.S.C. 371 of PCT/EP98/05710 filed Sep. 1, 1998, which claims priority from EP 97.202.761.9, filed Sep. 8, 1997

The present invention concerns tetrahydro γ-carbolines having a broad therapeutic potential. It further relates to their preparation, compositions comprising them and their use as a medicine.

U.S. Pat. No. 4,636,563, published on Jan. 13, 1987, and U.S. Pat. No. 4,672,117, published on Jun. 9, 1987, disclose 2-(heteroaryl-alkyl)-tetrahydro-γ carbolines having antipsychotic activity. EP-A-0,705,832, published on Apr. 10, 1996, discloses 1,2,3,4-terahydro-9H-pyrido3,4-b]indolyl-alkyl-1,3-dihydro-2H-benzimidazolones as serotonergic modulators.

The compounds of the present invention are novel and have an interesting broad-spectrum receptor-binding profile. In comparison to the structurally related known compounds, they surprisingly exhibit a greater therapeutic breadth.

The present invention concerns the compounds of formula (I)

the N-oxide forms, the pharmaceutically acceptable addition salts and the stereochemically isomeric forms thereof, wherein:

$R^1$ is hydrogen, $C_{1-6}$alkyl, aryl or $C_{1-6}$alkyl substituted with aryl;

$R^2$ is each independently a halogen, hydroxy, $C_{1-6}$alkyl, $C_{1-6}$alkyloxy or nitro;

n is 0, 1, 2 or 3;

Alk is $C_{1-6}$alkanediyl;

D is 2(3H)benzoxazolone-3-yl or a radical of formula wherein
each X independently represents O, S or $NR^{12}$;

$R^3$ is hydrogen, $C_{1-6}$alkyl, aryl or $arylC_{1-6}$alkyl;

$R^4$ is hydrogen, $C_{1-6}$alkyl, $C_{1-6}$alkyloxy, $C_{1-6}$alkylthio, amino, mono- or di($C_{1-6}$alkyl)amino or mono- or di($arylC_{1-6}$alkyl)amino;

$R^5$, $R^6$, $R^7$, $R^{10}$, $R^{11}$ and $R^{12}$ each independently are hydrogen or $C_{1-6}$alkyl;

$R^8$ and $R^9$ each independently are hydrogen, $C_{1-6}$alkyl or aryl; or $R^4$ and $R^5$ taken together may form a bivalent radical $-R^4-R^5-$ of formula

| | |
|---|---|
| $-CH_2-CH_2-CH_2-$ | (a-1); |
| $-CH_2-CH_2-CH_2-CH_2-$ | (a-2); |
| $-CH=CH-CH_2-$ | (a-3); |
| $-CH_2-CH=CH-$ | (a-4) or |
| $-CH=CH-CH=CH-$ | (a-5); | wherein one or two hydrogen atoms of said radicals (a-1) to (a-5) each independently may be replaced by halogen, $C_{1-6}$alkyl, $arylC_{1-6}$alkyl, trifluoromethyl, amino, hydroxy, $C_{1-6}$alkyloxy or $C_{1-10}$alkylcarbonyloxy; or where possible, two germinal hydrogen atoms may be replaced by $C_{1-6}$alkylidene or $arylC_{1-6}$alkylidene; or $-R^4-R^5-$ may also be

| | |
|---|---|
| $-S-CH_2-CH_2-$ | (a-6); |
| $-S-CH_2-CH_2-CH_2-$ | (a-7); |
| $-S-CH=CH-$ | (a-8); |
| $-NH-CH_2-CH_2-$ | (a-9); |
| $-NH-CH_2-CH_2-CH_2-$ | (a-10); |
| $-NH-CH=CH-$ | (a-11); |
| $-NH-CH=N-$ | (a-12); |
| $-S-CH=N-$ | (a-13) or |
| $-CH=CH-O-$ | (a-14); | wherein one or where possible two or three hydrogen atoms in said radicals (a-6) to (a-14) each independently may be replaced by $C_{1-6}$alkyl or aryl; and aryl is phenyl or phenyl substituted with a halogen or $C_{1-6}$alkyl.

As used in the foregoing definitions the term halogen is generic to fluoro, chloro, bromo and iodo. The term $C_{1-4}$alkyl defines straight and branched saturated hydrocarbons, having from 1 to 4 carbon atoms such as, for example, methyl, ethyl, propyl, butyl, 1-methylethyl, 1,1-dimethylethyl, 2-methylpropyl and the like. The term $C_{1-6}$alkyl is meant to include $C_{1-4}$alkyl and the higher homologues thereof having 5 or 6 carbon atoms such as, for example, pentyl, hexyl or the like. The term $C_{1-10}$alkyl is meant to include $C_{1-6}$alkyl radicals and the higher homologues thereof having 7 to 10 carbon atoms such as, for example, heptyl, octyl, nonyl, decyl and the like. The term $C_{1-4}$alkanediyl defines bivalent straight or branch chained alkanediyl radicals having from 1 to 4 carbon atoms such as, for example, methylene, 1,2-ethanediyl, 1,3-propanediyl, 1,4-butanediyl and the like; the term $C_{1-6}$alkanediyl is meant to include $C_{1-4}$alkanediyl and the higher homologues thereof having 5 or 6 carbon atoms such as, for example, 1,5-pentanediyl, 1,6-hexanediyl and the like; the term $C_{1-6}$alkylidene defines bivalent straight or branch chained alkylidene radicals having from 1 to 6 carbon atoms such as, for example, methylene, ethylidene, 1-propylidene, 1-butylidene, 1-pentylidene, 1-hexylidene and the like.

Also as used hereinafter, the term benzyl refers to phenylmethyl. Other names for the term γ-carboline are 5H-pyrido[4,3-b]indole, 3-azacarbazole and 3-azarbazole.

The addition salts as mentioned herein are meant to comprise the therapeutically active addition salt forms which the compounds of formula (I) are able to form with appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The pharmaceutically acceptable addition salts as mentioned hereinabove are also meant to comprise the therapeutically active non-toxic base, in particular, a metal or amine addition salt forms which the compounds of formula (I) are able to form. Said salts can conveniently be obtained by treating the compounds of formula (I) containing acidic hydrogen atoms with appropriate organic and inorganic bases such as, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said salt forms can be converted by treatment with an appropriate base or acid into the free acid or base form.

The term addition salt as used hereinabove also comprises the solvates which the compounds of formula (I) are able to form and said solvates are meant to be included within the scope of the present invention. Examples of such solvates are, e.g. the hydrates, alcoholates and the like.

The N-oxide forms of the compounds of formula (I) are meant to comprise those compounds of formula (I) wherein one or several nitrogen atoms are oxidized to the so-called N-oxide.

The term stereochemically isomeric forms as used herein defines all the possible isomeric forms in which the compounds of formula (I) may occur. Unless otherwise mentioned or indicated, the chemical designation of compounds denotes the mixture of all possible stereochemically isomeric forms, said mixtures containing all diastereomers and enantiomers of the basic molecular structure.

Some of the compounds of formula (I) may also exist in their tautomeric forms. Such forms although not explicitly indicated in the above formula are intended to be included within the scope of the present invention.

Whenever used hereinafter, the term compounds of formula (I) is meant to include also the N-oxide forms, the pharmaceutically acceptable addition salts and all stereoisomeric forms.

A special group of compounds includes those compounds of formula (I) wherein one or more of the following restrictions apply:

1) $R^2$ is halogen, hydroxy, $C_{1-6}$alkyl or $C_{1-6}$alkyloxy;
2) n is 0 or 1;
3) Alk is $C_{1-4}$alkanediyl; preferably, Alk is 1,2-ethanediyl;
4) D is a radical of formula (a) wherein $R^3$ is $C_{1-6}$alkyl, aryl or aryl$C_{1-6}$alkyl; $R^4$ is amino, mono- or di($C_{1-6}$alkyl)amino, or mono- or di(aryl$C_{1-6}$alkyl)amino; or —$R^4$—$R^5$— is a radical of formula (a-2) or (a-5) wherein one or two hydrogen atoms each independently may be replaced by halogen, $C_{1-6}$alkyl, trifluoromethyl or $C_{1-6}$alkyloxy, or —$R^4$—$R^5$— is a radical of formula (a-6), (a-7), (a-8), (a-11), (a-13) or (a-14) wherein one or where possible two hydrogen atoms each independently may be replaced by $C_{1-6}$alkyl;
5) D is a radical of formula (b) and $R^6$ and $R^7$ are suitably methyl;
6) D is a radical of formula (c) and $R^8$ is suitably hydrogen, methyl or phenyl;
7) D is a radical of formula (d) wherein $R^9$ is aryl; and suitably, $R^9$ is 4-fluoro-phenyl, and the piperidine ring is connected in the 3- or 4-position to the remainder of the molecule;
8) D is a radical of formula (e) wherein X is S or NH and $R^{10}$ is hydrogen; or
9) D is a radical of formula (f) wherein X is S or $NCH_3$.

In case n is 1, the $R^2$ substituent is suitably positioned in the 6-, 7- or 8-position of the γ-carboline moiety, preferably in the 7- or 8-position, and $R^2$ is preferably chloro, fluoro, methyl, hydroxy or methoxy.

Suitably, D is a radical of formula (a), (d), (e) or (f).

An interesting group of compounds includes those compounds of formula (I) wherein $R^1$ is hydrogen or aryl; $R^2$ is halogen or $C_{1-6}$alkyl; n is 0 or 1; Alk is $C_{1-4}$alkanediyl; D is a radical of formula (a) or (e), especially a radical of formula (a) wherein $R^3$ is $C_{1-6}$alkyl and —$R^4$—$R^5$— is a radical of formula (a-2), (a-5), (a-6), (a-7) or (a-8) wherein one or where possible two hydrogen atoms each independently may be replaced by $C_{1-6}$alkyl, or a radical of formula (e) wherein X is S and $R^{10}$ is hydrogen.

Another interesting group of compounds includes those compounds of formula (I) wherein $R^1$ is hydrogen or $C_{1-6}$alkyl; $R^2$ is halogen, $C_{1-6}$alkyl or $C_{1-6}$alkyloxy; n is 0 or 1; Alk is $C_{1-4}$alkanediyl; D is a radical of formula (a) or (f), especially a radical of formula (a) wherein $R^4$ is amino, mono- or di($C_{1-6}$alkyl)amino or mono- or di(aryl$C_{1-6}$alkyl)amino, or —$R^4$—$R^5$— is a radical of formula (a-2), (a-5), (a-6), (a-7), (a-8) or (a-11) wherein one or where possible two hydrogen atoms each independently may be replaced by $C_{1-6}$alkyl or a radical of formula (f) wherein X is $NR^{12}$.

Yet another interesting group of compounds includes those compounds of formula (I) wherein $R^2$ is halogen, hydroxy, $C_{1-6}$alkyl or $C_{1-6}$alkyloxy; n is 0 or 1, Alk is $C_{1-4}$alkanediyl; D is a radical of formula (a), (e) or (f), especially a radical of formula (a) wherein $R^3$ is $C_{1-6}$alkyl, $R^4$ is amino, or —$R^4$—$R^5$— is a radical of formula (a-2) or (a-5) wherein one or two hydrogen atoms each independently may be replaced by halogen, $C_{1-6}$alkyl, trifluoromethyl or $C_{1-6}$alkyloxy, or —$R^4$—$R^5$— is a radical of formula (a-6), (a-7), (a-8), (a-11), (a-13) or (a-14) wherein one or where possible two hydrogen atoms each independently may be replaced by $C_{1-6}$alkyl, or a radical of formula (e) wherein X is S or $NR^{12}$ and $R^{10}$ is hydrogen, or a radical of formula (f) wherein X is S or $NR^{12}$.

Still another interesting group of compounds includes those compounds of formula (I) wherein $R^1$ is hydrogen, $C_{1-6}$alkyl or aryl; $R^2$ is halogen, $C_{1-6}$alkyl or $C_{1-6}$alkyloxy; n is 0 or 1; Alk is $C_{1-4}$alkanediyl; D is a radical of formula (a), (d) or (e), especially a radical of formula (a) wherein $R^3$ is $C_{1-6}$alkyl or aryl$C_{1-6}$alkyl, or —$R^4$—$R^5$— is a radical of formula (a-5) wherein one or two hydrogen atoms each independently may be replaced by a halogen, or —$R^4$—$R^5$— is a radical of formula (a-6) or (a-8), or a radical of formula (d) wherein $R^9$ is aryl, or a radical of formula (e) wherein X is S or $NR^{12}$ and $R^{10}$ is hydrogen.

Particular compounds are those compounds of formula (a) wherein $R^1$ is hydrogen; n is 0 or n is 1 whereby $R^2$ is a halogen, $C_{1-6}$alkyl, or $C_{1-6}$alkoxy; Alk is 1,2-ethanediyl and D is a radical of formula (a) or (f), especially a radical of formula (a) wherein $R^3$ is $C_{1-6}$alkyl, $R^4$ is amino, $R^5$ is $C_{1-6}$alkyl, or —$R^4$—$R^5$— is a radical of formula (a-2), (a-5), (a-6) (a-7), (a-8) or (a-11) wherein one hydrogen atom may be replaced by $C_{1-6}$alkyl, or a radical of formula (f) wherein X is $NR^{12}$ and $R^{11}$ is $C_{1-6}$alkyl; more in particular, wherein $R^1$ is hydrogen; n is 0 or n is 1 whereby $R^2$ is a chloro, methyl, or methoxy; Alk is 1,2-ethanediyl and D is a radical of formula (a) wherein $R^3$ is methyl, $R^4$ is amino, $R^5$ is methyl, or —$R^4$—$R^5$— is a radical of formula (a-2), (a-5), (a-6), (a-7), (a-8) or (a-11) wherein one hydrogen atom may be replaced by methyl, or D is a radical of formula (f) wherein X is N—$CH_3$ and $R^{11}$ is methyl.

Other particularly interesting compounds are those compounds of formula (I) wherein $R^1$ is hydrogen; n is 0 or n is 1 whereby $R^2$ is a halogen or $C_{1-6}$alkyl; Alk is 1,2-ethanediyl and D is a radical of formula (a), especially a radical of formula (a) wherein $R^3$ is $C_{1-6}$alkyl, $R^4$ and $R^5$ are taken together to form —$R^4$—$R^5$— of formula (a-2), (a-5), (a-6), (a-7) or (a-8) wherein one hydrogen atom may be replaced by $C_{1-6}$alkyl; more in particular, wherein $R^1$ is hydrogen; n is 0 or n is 1 whereby $R^2$ is a chloro, fluoro or methyl; Alk is 1,2-ethanediyl and D is a radical of formula (a) wherein $R^3$ is methyl, $R^4$ and $R^5$ are taken together to form —$R^4$—$R^5$— of formula (a-2), (a-5), (a-6), (a-7) or (a-8) wherein one hydrogen atom may be replaced by methyl.

A preferred set of compounds includes those compounds of formula (1) wherein $R^1$ is hydrogen, methyl, n-butyl, phenyl, benzyl or 4-fluoro-phenyl.

The compounds of formula (I) can generally be prepared by N-alkylating a 1,3,4,5-tetrahydro-2H-pyrido[4,3-b]indole derivative of formula (II) with an alkylating reagent of formula (III) following the procedure described in EP-A-0,037,265, EP-A-0,070,053, EP-A-0,196,132 and in EP-A-0,378,255.

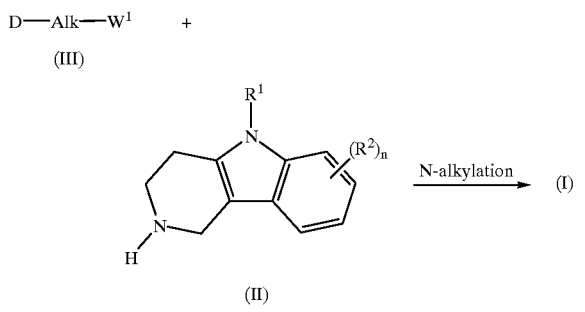

In particular, intermediate (III) wherein $W^1$ represents an appropriate reactive leaving group such as, for example, a halogen, e.g. chloro, bromo or iodo; a sulfonyloxy, e.g. methanesulfonyloxy, toluenesulfonyloxy, may be reacted with an intermediate of formula (II) in a reaction-inert solvent such as, for example, N,N-dimethylformamide or methylisobutylketon, in the presence of a suitable base such as, for example, sodiumcarbonate or triethylamine, and optionally in the presence of a catalyst such as, for example, potassium iodide.

In this and the following reactions, the reaction products may be isolated from the reaction medium and, if necessary, further purified according to methodologies generally known in the art such as extraction, crystallization, trituration and chromatography.

The compounds of formula (I) wherein D is a radical of formula (e), being represented by formula (I-e), may be prepared by N-acylating an intermediate of formula (IV) with an acyl derivative of formula (V) wherein $W^2$ is an appropriate reactive leaving group such as, for example, a halogen, in a reaction-inert solvent such as, for example, chloroform, in the presence of a suitable base such as, for example, sodium carbonate or triethylamine.

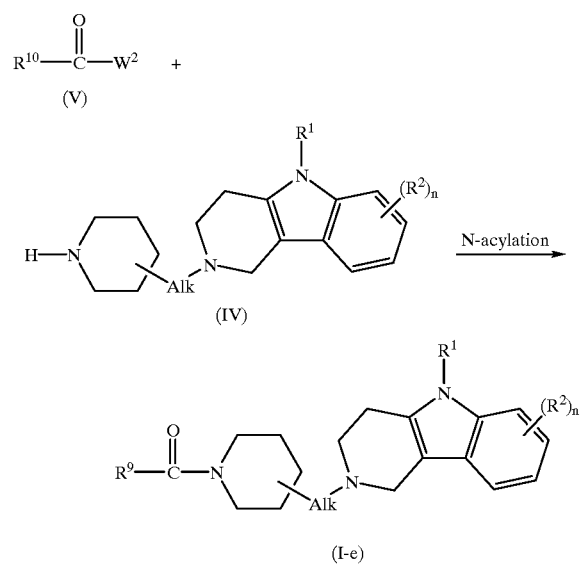

The compounds of formula (I) wherein D is a radical of formula (f), being represented by formula (I-f), can be prepared by N-alkylating an amine of formula (VI) with an intermediate of formula (VII) wherein $W^3$ is an appropriate reactive leaving group such as, for example, a halogen, in a reaction-inert solvent such as, for example, ethanol or toluene, in the presence of a suitable base such as, for example, sodiumbicarbonate or sodiumcarbonate.

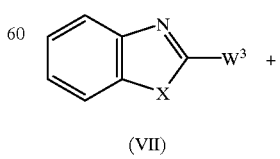

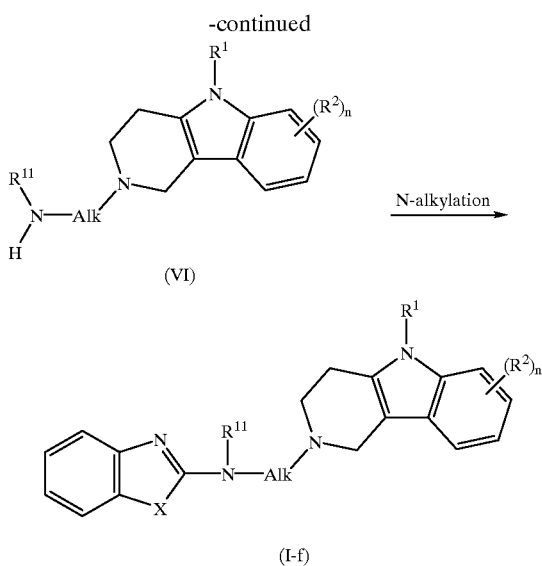

Alternatively, intermediates (VI) may be N-alkylated with intermediates (VII) in the presence of copper.

The compounds of formula (I) may be converted into each other following art-known functional group transformation reactions.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

A number of intermediates and starting materials are commercially available or are known compounds which may be prepared according to art-known methodologies.

For example, some of the intermediates of formula (III) and their preparations are described in EP-A-0,037,265, EP-A-0,070,053, EP-A-0,196,132 and in EP-A-0,378,255.

Intermediates of formula (11) wherein RI is hydrogen, said intermediates being represented by formula (II-a), can generally be prepared by reacting an intermediate of formula (VIII) wherein P is a protective group such as, for example, an alkyloxy-carbonyl group, with an intermediate of formula (IX) in a reaction-inert solvent, thus forming an intermediate of formula (X), and subsequently removing the protective group using art-known techniques such as, for instance, mixing the intermediate of formula (X) with potassium hydroxide in 2-propanol. Alternatively, the intermediate of formula (X) may be further reacted with a reagent of formula (XI) wherein $R^{1'}$ is the same as $R^1$ but other than hydrogen and $W^4$ is a suitable leaving group such as, for example, a halogen, in a suitable solvent such as, for example, hexamethylphosphorous triamide and the like, in the presence of an appropriate base such as, for example, sodium hydride, thus forming an intermediate of formula (XII) which may subsequently be deprotected using art-known techniques resulting in a compound of formula (II) wherein $R^1$ is other than hydrogen, said compounds being represented by formula (II-b).

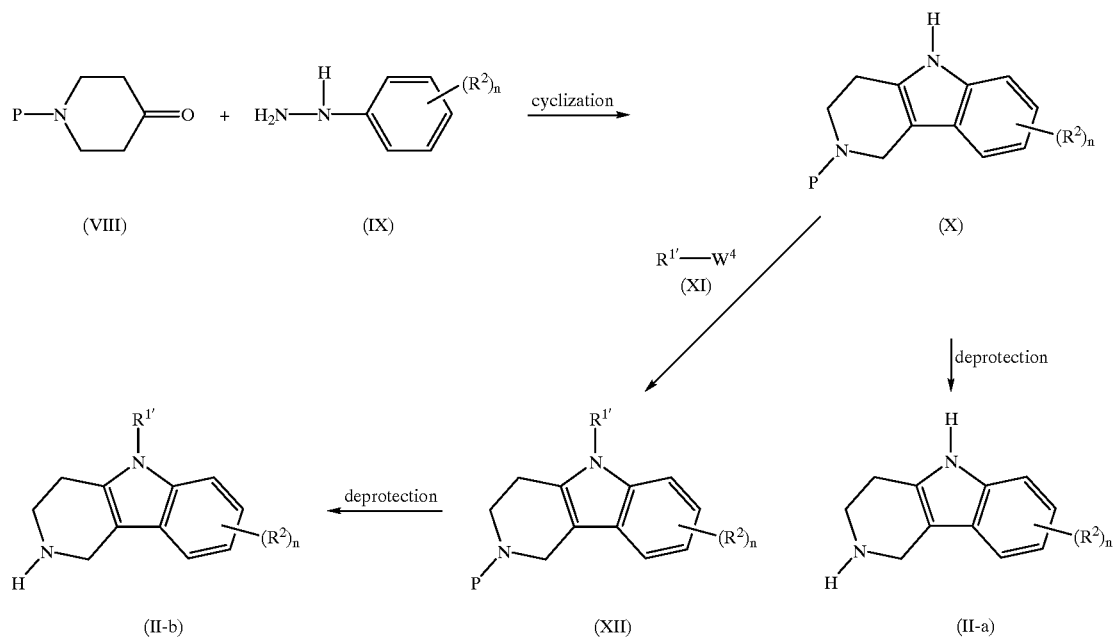

Intermediates of formula (IV) can be prepared by N-alkylating an intermediate of formula (II) with an intermediate of formula (XIII) wherein P is a protective group such as, for example, an alkyloxycarbonyl group, and $W^5$ is a suitable leaving group such as, for example, ap-toluenesulfonyloxy group and the like, in a reaction-inert solvent such as, for example, N,N-dimethylformamide, and in the presence of a suitable base such as, for example, sodium carbonate. The thus formed intermediate may be deprotected using art-known deprotection techniques.

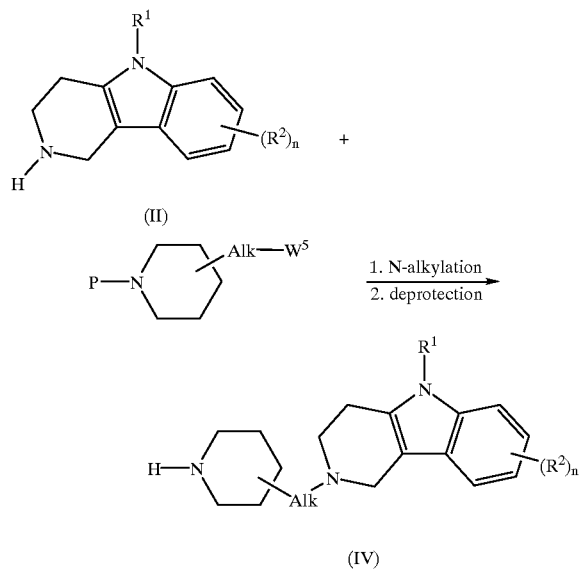

Intermediates of formula (VI) may be prepared by N-alkylating an intermediate of formula (II) with an intermediate of formula (XIV) wherein P is a protective group such as, for example, an alkyloxycarbonyl group, and $W^6$ is a suitable leaving group such as, for example, a halogen, in a reaction-inert solvent such as, for example, methylisobutylketon, in the presence of a suitable base such as, for example, sodium carbonate, and optionally in the presence of a catalyst such as, for instance, potassium iodide. The thus formed intermediate may be deprotected using art-known deprotection techniques.

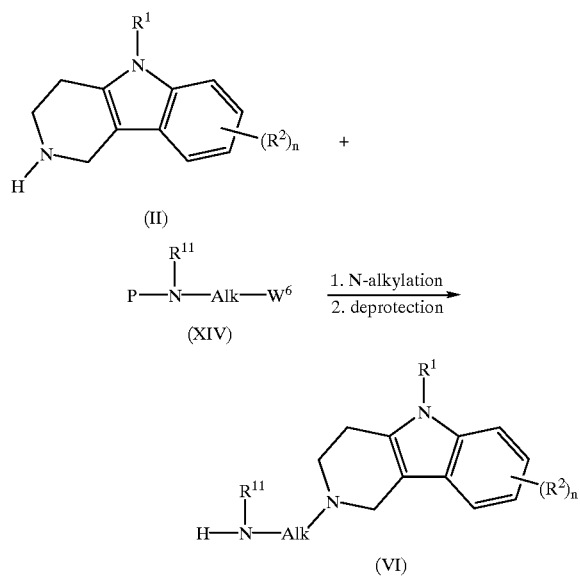

Intermediates of formula (VI) wherein Alk is 1,3-propanediyl and $R^{11}$ is hydrogen, said intermediates being represented by formula (VI-3) may suitably be prepared by reacting an intermediate of formula (II) with acrylonitrile in a reaction-inert solvent such as, for example, 2-propanol, and in the presence of a suitable catalyst such as, for example, a quaternary ammonium compound, e.g. Aliquat 336, thus forming a nitrile derivative of formula (XV) which may subsequently be reduced to the corresponding amine derivative using art-known reduction techniques as there are, for example, the use of hydrogen with Raney Nickel as a catalyst in methanol, optionally in the presence of ammonia.

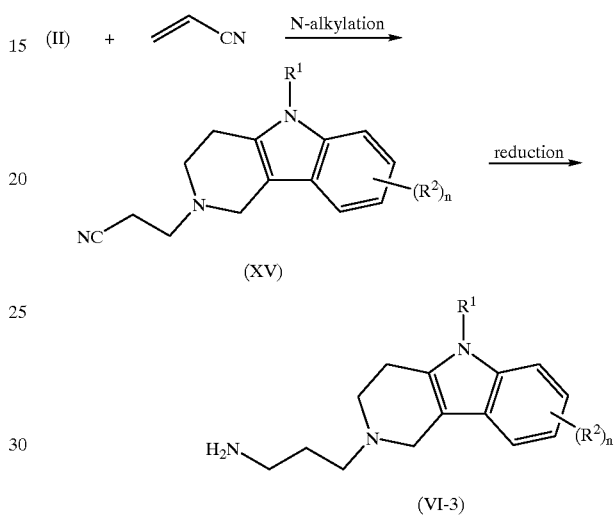

Intermediates of formula (VI) wherein Alk is 1,4-butanediyl and $R^{11}$ is hydrogen, said intermediates being represented by formula (VI-4) may suitably be prepared by reacting an intermediate of formula (II) with an intermediate of formula (XVI) wherein $W^7$ is a suitable leaving group such as, for example a halogen, in a reaction-inert solvent such as, for example, methylisobutylketon, and in the presence of a suitable base such as, for example, sodium carbonate, and optionally in the presence of a catalyst such as, for instance, potassium iodide, thus forming a nitrile derivative of formula (XVII) which may subsequently be reduced to the corresponding amine derivative using art-known reduction techniques as there are, for example, the use of hydrogen with Raney Nickel as a catalyst in methanol, optionally in the presence of ammonia.

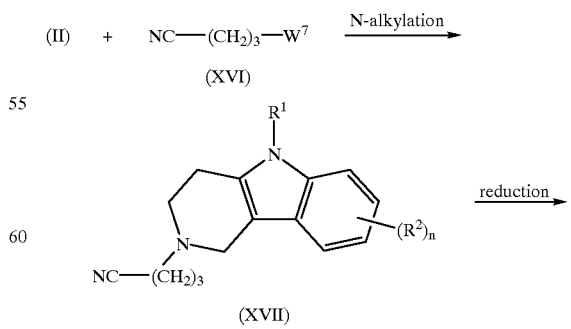

-continued

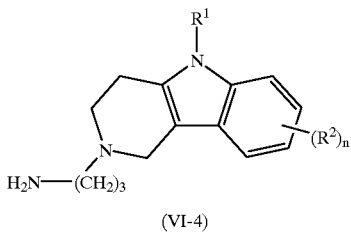

(VI-4)

Some of the compounds of formula (I) and some of the intermediates in the present invention contain at least one asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers.

Pure stereochemically isomeric forms of the compounds of formula (I) may also be obtained from the pure stereochemically isomeric forms of the appropriate intermediates and starting materials, provided that the intervening reactions occur stereospecifically. The pure and mixed stereochemically isomeric forms of the compounds of formula (I) are intended to be embraced within the scope of the present invention.

The compounds of formula (I), their pharmaceutically acceptable addition salts, stereochemically isomeric forms, or N-oxide forms thereof, all show a particular affinity for serotonin receptors, such as, 5-hydroxytryptamine receptors of the $5HT_1$- and $5\text{-}HT_2$-type, and have an antagonistic, partially antagonistic or agonistic effect thereon. Apart from their serotonergic receptor affinity, the present compounds also bind as ligands on the $\alpha_2$- or dopamine receptors, or selectively inhibit serotonin reuptake. This broad-spectrum receptor-binding profile of the present compounds gives them a great therapeutic breadth. They are useful in controlling diseases which are characterized by disturbances of the serotonergic system, in particular with involvement of $5HT_2$-type receptors. They are therefore suitable for treating disorders of the central nervous system including psychotic disorders such as, e.g. schizophrenia, tension and depression states, neuroses, psychoses, bipolar disorders, aggressive behaviour, anxiety and the like. Further, serotonin is a potent broncho- and vasoconstrictor and thus the present compounds acting as antagonists on the serotonin receptors may also be used against hypertension and vascular disorders such as, migraine and migraine related disorders. Compounds controlling the serotonergic system have been associated with a number of other properties such as, the suppression of appetite and promotion of weight loss, which may prove effective in combatting obesity; the alleviation of withdrawal symptoms in addicts trying to discontinue drinking and smoking habits; and also with gastrointestinal disorders such as, e.g. colonkinetic disturbances.

Also the inhibitory activity of a particular group of the present compounds on the reuptake of serotonin contributes to the effectiveness to treat tension and depression states.

An additional feature of the present compounds is that they have central $\alpha_2$-adrenoceptor antagonistic activity. Central $\alpha_2$-adrenoceptor antagonists are known to increase noradrenaline release by blocking presynaptic $\alpha_2$-receptors which exert an inhibiting control over the release of the neurotransmitter. By increasing the noradrenaline concentrations, $\alpha_2$-antagonists can be used particularly for the treatment or prophylaxis of depression, and are also potentially useful in the treatment of Alzheimer's disease and dementia as it is known that $\alpha_2$-antagonists promote the release of acetylcholine (Tellez et al. 1997, J. Neurochem. 68:778–785).

A particular group of the present compounds exhibits a pronounced affinity for dopaminergic receptors which in combination with an affinity for serotonergic receptors is of therapeutic significance in the treatment of psychosis.

The $5\text{-}HT_2$ receptor-binding profile of the compounds of formula (I) is discussed in the pharmacological example C.1. The binding profile for other receptors such as, the $\alpha_2$-adrenergic or the dopaminergic receptors, may be demonstrated using analogous radioligand binding studies. Further, the serotonergic properties of the present compounds may be evidenced by the "apomorphine, tryptamine, norepinephrine (ATN) test in rats", described in Arch. Int. Pharmacodyn., 227, 238–253 (1977).

The present invention thus relates to compounds of formula (I) as defined hereinabove for use as a medicine. Also, the present invention relates to the use of the present compounds for the manufacture of a medicament for treating depression, anxiety and psychosis.

In view of the usefulness of the subject compounds in the treatment or prevention of the above-mentioned disorders, the present invention provides a method of treating warm-blooded animals suffering from such disorders, in particular depression, anxiety and psychosis, said method comprising the systemic administration of a therapeutic effective amount of a compound of formula (I), a N-oxide or a pharmaceutically acceptable addition salt thereof, effective in treating disorders associated with the serotonergic system In general it is contemplated that an effective therapeutic daily amount would be from about 0.01 mg/kg to about 4 mg/kg body weight. The exact dosage to be used in the treatment of any of the above-mentioned disorders must be subjectively determined by the attending physician. The variables involved include the severity of the disorder and the size, age and response pattern of the patient.

For administration purposes, the subject compounds may be formulated into various pharmaceutical compositions comprising a pharmaceutically acceptable carrier and, as active ingredient, a therapeutically effective amount of a compound of formula (I). To prepare the pharmaceutical compositions of this invention, an effective amount of the particular compound, in addition salt or in free acid or base form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable f or percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Addition salts of (I) due to their increased water solubility over the corresponding free base or free acid form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutic al carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following examples are intended to illustrate the present invention.

Experimental Part

A. Preparation of the Intermediates

EXAMPLE A1 a) A mixture of ethyl 4-oxo-1-piperidinecarboxylate (0.23 mol ) and 4-(benzyloxy)-phenyl hydrazine (0.23 mol) in ethanol (400 ml) was stirred and refluxed for 5 hours . The reaction mixture was stirred overnight at room temperature. The solid was filtered off and washed on filter with $H_2O$/2-propanol (200 ml). The precipitate was dissolved in $CHCl_3$ (300 ml), washed with water (2×50 ml), dried, filtered and the solvent was evaporated. The residue was crystallized from $CH_3CN$ (300 ml) and cooled to 0° C. The resulting precipitate was filtered off and dried, yielding 51.0 g (63%) of ethyl 1,3,4,5-tetrahydro-8-(phenylmethoxy)-2H-pyrido [4,3-b] indole-2-carboxylate (intermediate 1).

b) A mixture of intermediate (1) (0.09 mol) in N,N-dimethylformamide (200 ml) was stirred at 10° C. under a $N_2$ flow. Sodium hydride (60%; 0.1 mol) was added portionwise. The mixture was stirred for 1 hour at room temperature, then it was cooled to 5° C. Benzylbromide (0.1 mol) was added dropwise. Stirring was continued for 2 hours. The mixture was cooled to 10° C. and poured out into cold water (500 ml). This mixture was extracted with $CH_2Cl_2$ (2×250 ml). The separated organic layer was washed with water (100 ml), dried, filtered and the solvent was evaporated. The solid residue was washed with $CH_3CN$ (50 ml), cooled and the resulting precipitate was filtered off and dried, yielding 30.0 g (76%) of ethyl 1,3,4,5-tetrahydro-8-(phenyl-methoxy)-5-(phenyl-methyl)-2H-pyrido[4,3-b]indole-2-carboxylate (intermediate 2).

c) A mixture of intermediate (2) (0.067 mol) and KOH (0.67 mol) in 2-propanol (250 ml) was stirred and refluxed for 5 hours. The solvent was evaporated. Water (300 ml) was added and the organic solvent was removed azeotropically. The precipitate was filtered off and dissolved in $CH_2Cl_2$ (300 ml). The organic solution was dried, filtered and the solvent was evaporated. The residue was washed in $CH_3CN$ (50 ml), filtered off and dried, yielding 22.7 g (92%) of 2,3,4,5-tetrahydro-8-(phenyl-methoxy)-5-(phenylmethyl)-1H-pyrido[4,3-b]indole (intermediate 3).

d) A mixture of intermediate (3) (0.062 mol) in methanol (400 ml) and tetrahydrofuran (100 ml) was warmed to 50° C. until complete dissolution. This solution was hydrogenated at 50° C. with palladium-on-charcoal (10%; 5 g) as a catalyst. After uptake of $H_2$ (1 equivalent), hydrogenation was stopped and acetic acid (50 ml) was added to dissolve the precipitate. The catalyst was filtered off and the filtrate was acidified with HCl/2-propanol (30 ml). The precipitate was filtered off, suspended in $CH_3CN$ (100 ml), filtered off and dried, yielding 14.5 g (74%) of 2,3,4,5-tetrahydro-5-(phenylmethyl)-1H-pyrido[4,3-b]indol-8-ol monohydrochloride (intermediate 8).

EXAMPLE A.2 a) A mixture of 2,3,4,5-tetrahydro-8-methyl-1H-pyrido[4,3-b]indole, (0.079 mol), ethyl 3-chloropropanamide (0.097 mol), $Na_2CO_3$ (15 g) and potassium iodide (0.1 g) in methyl isobutyl ketone (350 ml) was stirred and refluxed overnight. The reaction mixture was filtered and the filtrate was evaporated, yielding 20 g (80%) of ethyl [3-(1,3,4,5-tetrahydro-8-methyl-2H-pyrido[4,3-b]indol-2-yl)propyl] carbamate (intermediate 10).

b) A mixture of intermediate (10) (0.063 mol) and KOH (35 g) in 2-propanol (300 ml) was stirred and refluxed overnight. The solvent was evaporated. The residue was stirred in water and this mixture was extracted with methyl isobutyl ketone. The separated organic layer was dried, filtered and the solvent evaporated. The residue was purified by column chromatography over silica gel (eluent: $CH_2Cl_2$/($CH_3OH/NH_3$) 85/15). The pure fractions were collected and the solvent was evaporated, yielding 7 g (46%) of 1,3,4,5-tetrahydro-8-methyl-2H-pyrido[4,3-b]indole-2-propanamine (intermediate 11).

EXAMPLE A.3 a) A mixture of 2,3,4,5-tetrahydro-5-methyl-1H-pyrido[4,3-b]indole (0.07mol), acrylonitrile (0.14 mol) and Aliquat 336 (3 drops) in $^2$-propanol (150 ml) was stirred and refluxed for 30 minutes. The reaction mixture was cooled on an ice-bath and the resulting precipitate was filtered off, washed with diisopropyl ether (50 ml) and dried, yielding 14.5 g (87%) of 1,3,4,5-tetrahydro-5-methyl-2H-pyrido[4,3-b] indole-2-propanenitrile (intermediate 15).

b) A mixture of intermediate (15) (0.06 mol) in $NH_3$/$CH_3OH$ (400 ml) was hydrogenated at 20° C. with Raney Nickel (3 g) as a catalyst. After uptake of hydrogen (2 equivalents), the catalyst was filtered off and the filtrate was evaporated, yielding 14.6 g of 1,3,4,5-tetrahydro-5-methyl-2H-pyrido[4,3-b]indole-2-propanamine (intermediate 16).

EXAMPLE A.4 a) A mixture of 1,2,3,4-tetrahydro-5H-pyrido[4,3-b]indole (0.2 mol) and 1-(phenyl-methyl)-4-piperidinone (0.2 mol) in methanol (700 ml) was hydrogenated at 50° C. with palladium-on-charcoal (10%; 3 g) as a catalyst in the presence of thiophene (4%; 2 ml). After uptake of hydrogen (1 equivalent), the catalyst was filtered off and the filtrate was evaporated, yielding 69 g 2,3,4,5-tetrahydro-2-[1-(phenylmethyl)-4-piperidinyl]-1H-pyrido [4,3-b]indole (intermediate 24).

b) A mixture of intermediate (24) (0.20 mol) in methanol (700 ml) was hydrogenated at 50° C. with palladium-on-charcoal (10%; 3 g) as a catalyst. After uptake of hydrogen (1 equivalent), the catalyst was filtered off and the filtrate was evaporated. The residue was crystallized from diisopropylether/CH$_3$CN. The precipitate was filtered off and dried yielding 44.1 g (86.4%) of 2,3,4,5-tetrahydro-2-(4-piperidinyl)-1H-pyrido [4,3,-b]indole (intermediate 25).

The following intermediates were prepared according to one of the above examples.

intermediate (9) (0.015 mol) and sodium carbonate 0.075 mol) in methylisobutyl ketone (250 ml) was stirred and refluxed for 18 hours. The mixture was filtered hot and the filtrate was evaporated. The residue was crystallized from N,N-dimethylformamide (20 ml). The precipitate was filtered off, washed on a filter with methanol (5 ml) and dried, yielding 0.8 g (14%) of 3,7-dimethyl-6-[2-(1,3,4,5-tetrahydro-8-hydroxy-2H-pyrido[4,3-b]indol-2-yl)ethyl ]-5H-thiazolo[3,2-a]pyrimidin-5-one (compound 59).

b) 7-[2-(8-fluoro-1,3,4,5-tetrahydro-2H-pyrido[4,3-b]indol-2-yl) ethyl]-3,4-dihydro-8-methyl-2H, 6H-pyrimido [2,1-b][1,3]-thiazin-6-one (compound 2) was prepared in a similar way as compound 59 but a catalytic amount of sodium methoxide (30% solution) was added to the reaction mixture.

c) 6,7,8,9-tetrahydro-2-methyl-3-[2-(1,3,4,5-tetrahydro-5-methyl-2H-pyrido [4,3-b]-indol-2-yl) ethyl]-4H-pyrido[1,2-a]pyrimidin-4-one (compound 81) was prepared in a similar way as compound 59 but a catalytic amount of potassium iodide was added to the reaction mixture.

d) (±)-1-(4-fluorobenzoyl)-3-[(1,3,4,5-tetrahydro-5-methyl-2H-pyrido[4,3-b]indol-2-ylmethyl]piperidine (E)-2-butenedioate (1:1) (compound 117) was prepared in a similar way as compound 59 but N,N-dimethylformamide was used as reaction-inert solvent instead of methylisobutylketon.

TABLE 1

| Interm. No. | Ex. No. | D | R$^1$ | R$^2$ | Physical data melting point in ° C. |
|---|---|---|---|---|---|
| 4 | A1c | H | CH$_3$ | H | HCl |
| 5 | A1c | H | (CH$_2$)$_3$—CH$_3$ | H | HCl |
| 6 | A1c | H | C$_6$H$_5$—CH$_2$— | H | HCl; mp. 242.5° C. |
| 7 | A1c | (CH$_2$)$_4$—NH$_2$ | H | 7-Cl | — |
| 9 | A1d | H | H | 8-OH | HCl |
| 12 | A2 | H—N⟨piperidine⟩—CH$_2$— | CH$_3$ | H | 100° C. |
| 13 | A2 | (CH$_2$)$_3$—NH$_2$ | H | 8-Cl | — |
| 14 | A2 | (CH$_2$)$_3$—NH$_2$ | H | 7-Cl | — |
| 17 | A3 | (CH$_2$)$_3$—NH$_2$ | H | H | — |
| 18 | A3 | (CH$_2$)$_4$—NH$_2$ | H | H | — |
| 19 | A3 | (CH$_2$)$_4$—NH$_2$ | H | 8-F | 108.4° C. |
| 20 | A3 | (CH$_2$)$_3$—NH$_2$ | H | 8-F | — |
| 21 | A3 | (CH$_2$)$_4$—NH$_2$ | H | 8-CH$_3$ | — |
| 22 | A3 | (CH$_2$)$_4$—NH$_2$ | H | 8-OCH$_3$ | — |
| 23 | A3 | (CH$_2$)$_3$—NH$_2$ | H | 8-OCH$_3$ | — |
| 26 | A1c | H—N⟨piperidine⟩—CH$_2$— | H | 8-F | — |

Preparation of the Compounds of Formula (I)

EXAMPLE B.1 a) mixture of 6-(2-bromoethyl)-3,7-dimethyl-5H-thiazolo [3,2-a]pyrimidin-5-one monohydrobromide (0.017 mol), e) 3-[2-(7-chloro-1,3,4,5-tetrahydro-2H-pyrido[4,3-b]indol-2-yl) ethyl]-9-methoxy-2-methyl-4H-pyrido [1,2-a]pyrimidin-4-one (compound 20) was prepared in a similar way as compound 59 but triethylamine was used instead of sodium carbonate.

f) 2,3-dihydro-7-methyl-6-[2-(1,3,4,5-tetrahydro-8-hydroxy-2H-pyrido [4,3-b]indol-2-yl)ethyl]-5H-thiazolo[3,2-a]pyrimidin-5-one (compound 62) was prepared in a similar way as compound 117 but triethylamine was used instead of sodium carbonate.

g) A mixture of 6-(2-chloroethyl)-2,7-dimethyl-5H-1,3,4-thiadiazolo[3,2-a]pyrimidin-5-one (4.2 g), 1,2,3,4-tetrahydro-5H-pyrido[4,3-b]indole (2.65 g), sodium bicarbonate (2 g), potassium iodide (0.1 g) in 1-butanol (122 ml) was refluxed for 20 hours. The reaction mixture was filtered while hot and the filtrate was evaporated. The residue was purified by column chromatography over silica gel (eluent: $CHCl_3/CH_3OH$ 95/5). The solvent of the desired fraction was evaporated and the residue was crystallized from acetonitrile, yielding 1.6 g (28.1%) of 6-[2-(1,3,4,5-tetrahydro-2H-pyrido [4,3-b]-indol-2-yl) ethyl]-2,7-dimethyl-5H-1,3,4-thiadiazolo[3,2-a]pyrimidin-5-one (compound 42).

h) (±)-1-(4-fluorobenzoyl)-3-[2-(1,3,4,5-tetrahydro-2H-pyrido[4,3-b ]indol-2-yl)-ethyl ]piperidine (E)-2-butenedioate (2:3) (compound 120) was prepared in a similar way as compound 59 but chloroform was used as reaction-inert solvent instead of methylisobutylketon.

EXAMPLE B.2

A mixture of intermediate 26 (0.01 mol) and triethylamine (0.011 mol) in chloroform (150 ml) was stirred at room temperature. 4-fluoro-benzoylchloride (0.011 mol) was added. The reaction mixture was stirred for 60 minutes at room temperature. Water (50 ml) was added and the mixture was stirred for 10 minutes. The organic layer was separated, dried, filtered and the solvent was evaporated. The residue was solidified in $CH_3CN$ (40 ml), filtered off and dried, yielding 2.7 g (66%) of (±)-1-(4-fluoro-benzoyl)-3-[(8-fluoro-1,3,4,5-tetrahydro-2H-pyrido[4,3-b]indol-2-yl)methyl]piperidine (compound 119).

EXAMPLE B.3 a) A mixture of 2-chloro-benzothiazole (0.02 mol), intermediate 18 (0.018 mol) and sodiumbicarbonate (0.040 mol) in ethanol (120 ml) was stirred and refluxed overnight. The mixture was cooled and filtered until clear. The filtrate was evaporated. The residue was purified by column chromatography over silica gel (eluent: $CH_2Cl_2/CH_3OH$ 90/10). The desired fractions were collected and the solvent was evaporated. The residue was crystallized from $CH_3CN$. The precipitate was filtered off and dried, yielding 3.4 g (50%) of N-2-benzothiazolyl-1,3,4,5-tetrahydro-2H-pyrido[4,3-b]indole-2-butanamine (compound 107).

b) N-2-benzothiazolyl-8-fluoro-1,3,4,5,-tetrahydro-2H-pyrido[4,3-b]indole-2-butanamine (compound 108) was prepared in a similar way as compound 107 but sodium carbonate was replaced by sodiumbicarbonate and ethanol was replaced by toluene.

EXAMPLE B.4

A mixture of 2-chloro-1H-benzimidazole (0.015 mol), intermediate 16 (0.015 mol) and copper (0.015 mol) was stirred in an oil bath at 180° C. The mixture was cooled and the product was dissolved in $CHCl_3$ (50 ml). The solution was filtered over dicalite and the filtrate was evaporated. The residue was purified by column chromatography over silica gel (eluent: $CHCl_3/(CH_3OH/NH_3)$ 95/5). The pure fractions were collected and the solvent was evaporated. The residue was dissolved in $CH_3CN$ (50 ml) and converted into the hydrochloric acid salt (1:2) with HCl/2-propanol. The salt was filtered off, washed on filter with cold $CH_3CN$ (20 ml), then dried, yielding 1.1 g (17%) of N-1H-benzimidazol-2-yl-1,3,4,5-tetrahydro-5-methyl-2H-pyrido [4,3-b]indole-2-propanamine dihydrochloride.hemihydrate (compound 105).

Tables 2 to 8 list compounds of formula (I) which were prepared according to one of the above examples as indicated in the column "Ex No.".

TABLE 2

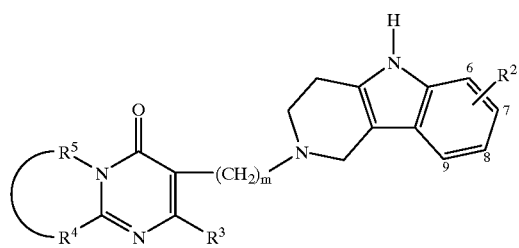

| Co. No. | Ex. No. | $R^2$ | $R^3$ | —$R^4$—$R^5$— | m | Physical data melting point in ° C. |
|---|---|---|---|---|---|---|
| 1 | B1c | 8-F | $CH_3$ | —CH=CH—CH=CH— | 2 | 225.5° C. |
| 2 | B1b | 8-F | $CH_3$ | —S—$CH_2$—$CH_2$—$CH_2$— | 2 | 208.3° C. |
| 3 | B1b | 8-F | $CH_3$ | —S—$CH_2$—$CH_2$— | 2 | 224.1° C. |
| 4 | B1c | 8-F | $CH_3$ | —$CH_2$—$CH_2$—$CH_2$—$CH_2$— | 2 | >300° C. |
| 5 | B1b | 8-F | $CH_3$ | —S—CH=C($CH_3$)— | 2 | 250.7° C. |
| 6 | B1c | 8-F | $CH_3$ | —S—CH=CH— | 2 | 218.1° C. |
| 7 | B1c | 7-Cl | $CH_3$ | —S—CH=CH— | 2 | 219.6° C. |
| 8 | B1b | 7-Cl | $CH_3$ | —S—CH=C($CH_3$)— | 2 | 199.2° C. |
| 9 | B1c | 7-Cl | $CH_3$ | —CH=CH—CH=CH— | 2 | 214.9° C. |
| 10 | B1c | 7-Cl | $CH_3$ | —$CH_2$—$CH_2$—$CH_2$—$CH_2$— | 2 | 202.4° C. |
| 11 | B1b | 7-Cl | $CH_3$ | —S—$CH_2$—$CH_2$—$CH_2$— | 2 | 227.0° C. |
| 12 | B1b | 7-Cl | $CH_3$ | —S—$CH_2$—$CH_2$— | 2 | 240.5° C. |
| 13 | B1c | 7-Cl | $CH_3$ | —C($CH_3$)=CH—CH=CH— | 2 | |

TABLE 2-continued

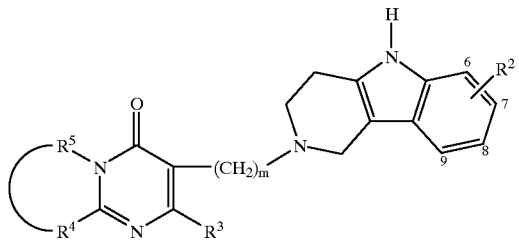

| Co. No. | Ex. No. | R² | R³ | —R⁴—R⁵— | m | Physical data melting point in ° C. |
|---|---|---|---|---|---|---|
| 14 | B1c | 7-Cl | CH₃ | —CH=CH—CBr=CH— | 2 | 296° C. |
| 15 | B1a | 7-Cl | CH₃ | —CCl=CH—C(CF₃)=CH— | 2 | 260° C. |
| 16 | B1c | 7-Cl | CH₃ | —CH=CH—C(CH₃)=CH— | 2 | |
| 17 | B1c | 7-Cl | CH₃ | —CH=CH—CCl=CH— | 2 | 278° C. |
| 18 | B1c | 7-Cl | CH₃ | —CH=C(CH₃)—CH=C(CH₃)— | 2 | 268° C.; fumaric acid |
| 19 | B1a | 7-Cl | CH₃ | —CCl=CH—CCl=CH— | 2 | 268° C. |
| 20 | B1e | 7-Cl | CH₃ | —C(OCH₃)=CH—CH=CH— | 2 | |
| 21 | B1c | 7-Cl | CH₃ | —CH=CH—CH=C(CH₃)— | 2 | |
| 22 | B1c | 7-Cl | CH₃ | —CH=C(CH₃)—CH=CH— | 2 | |
| 23 | B1b | 8-Cl | CH₃ | —S—CH=C(CH₃)— | 2 | 230.4° C. |
| 24 | B1b | 8-Cl | CH₃ | —S—CH₂—CH₂—CH₂— | 2 | 241.2° C. |
| 25 | B1c | 8-Cl | CH₃ | —S—CH=CH— | 2 | 215.8° C. |
| 26 | B1b | 8-Cl | CH₃ | —S—CH₂—CH₂— | 2 | 218.3° C. |
| 27 | B1c | 8-Cl | CH₃ | —CH₂—CH₂—CH₂—CH₂— | 2 | 217.1° C. |
| 28 | B1c | 8-Cl | CH₃ | —CH=CH—CH=CH— | 2 | 273.4° C. |
| 29 | B1c | 6-CH₃ | CH₃ | —S—CH₂—CH₂—CH₂— | 2 | 204.7° C. |
| 30 | B1c | 8-CH₃ | CH₃ | —S—CH=CH— | 2 | 197.9° C. |
| 31 | B1c | 8-CH₃ | CH₃ | —S—CH₂—CH₂— | 2 | 153.8° C.; H₂O(2:1) |
| 32 | B1c | 8-CH₃ | CH₃ | —S—CH=C(CH₃)— | 2 | 213.4° C. |
| 33 | B1c | 8-CH₃ | CH₃ | —S—CH₂—CH₂—CH₂— | 2 | 216.9° C. |
| 34 | B1c | 8-CH₃ | CH₃ | —CH=CH—CH=CH— | 2 | 209.8° C. |
| 35 | B1c | 8-CH₃ | CH₃ | —CH₂—CH₂—CH₂—CH₂— | 2 | 192.8° C. |
| 36 | B1c | 8-CH₃ | CH₃ | —CH₂—CH₂—CH₂—CH₂— | 2 | fumaric acid |
| 37 | B1c | H | CH₃ | —CH=CH—CH=CH— | 2 | 193.4° C. |
| 38 | B1c | H | CH₃ | —S—CH=CH— | 2 | 212.8° C. |
| 39 | B1a | H | CH₃ | —S—CH=C(CH₃)— | 2 | 274.1° C. |
| 40 | B1c | H | CH₃ | —CH₂—CH₂—CH₂—CH₂— | 2 | 189.1° C. |
| 41 | B1a | H | CH₃ | —S—CH₂—CH₂— | 2 | 208.3° C. |
| 42 | B1g | H | CH₃ | —S—C(CH₃)=N— | 2 | 270.2° C. |
| 43 | B1c | H | CH₃ | —N(CH₃)—CH=CH— | 2 | 229.9° C. |
| 44 | B1a | H | CH₃ | —S—CH₂—CH₂—CH₂— | 3 | 209.2° C. |
| 45 | B1a | H | CH₃ | —S—CH₂—CH₂— | 3 | 186.7° C. |
| 46 | B1a | H | CH₃ | —S—CH=C(CH₃)— | 3 | 178.6° C. |
| 47 | B1c | H | CH₃ | —C(CH₃)=CH—CH=CH— | 3 | 200.2° C. |
| 48 | B1a | H | CH₃ | —CH=CH—CH=CH— | 3 | |
| 49 | B1a | H | CH₃ | —S—CH=CH— | 3 | fumaric acid(2:1) |
| 50 | B1c | H | phenyl | —CH=CH—CH=CH— | 2 | 188.2° C. |
| 51 | B1c | H | benzyl | —CH=CH—CH=CH— | 2 | 193.5° C. |
| 52 | B1c | 8-OCH₃ | CH₃ | —CH₂—CH₂—CH₂—CH₂— | 2 | 202.3° C. |
| 53 | B1c | 8-OCH₃ | CH₃ | —CH=CH—CH=CH— | 2 | 173.1° C. |
| 54 | B1b | 8-OCH₃ | CH₃ | —S—CH=C(CH₃)— | 2 | 274.5° C. |
| 55 | B1b | 8-OCH₃ | CH₃ | —S—CH₂—CH₂— | 2 | 189.2° C. |
| 56 | B1b | 8-OCH₃ | CH₃ | —S—CH₂—CH₂—CH₂— | 2 | 235.7° C. |
| 57 | B1c | 8-OCH₃ | CH₃ | —S—CH=CH— | 2 | 141.5° C. |
| 58 | B1c | 8-OH | CH₃ | —CH=CH—CH=CH— | 2 | 219.2° C. |
| 59 | B1a | 8-OH | CH₃ | —S—CH=C(CH₃)— | 2 | 254.6° C. |
| 60 | B1c | 8-OH | CH₃ | —CH₂—CH₂—CH₂—CH₂— | 2 | 214.1° C. |
| 61 | B1c | 8-OH | CH₃ | —S—CH=CH— | 2 | 198.7° C. |
| 62 | B1f | 8-OH | CH₃ | —S—CH₂—CH₂— | 2 | 243.2° C. |
| 63 | B1f | 8-OH | CH₃ | —S—CH₂—CH₂—CH₂— | 2 | 218.6° C. |
| 64 | B1c | 8-OH | CH₃ | —CH=CH—CH=CH— | 3 | 207.5° C. |
| 65 | B1c | 8-OH | CH₃ | —CH=C(CH₃)—O— | 2 | 168.9° C. |

TABLE 3

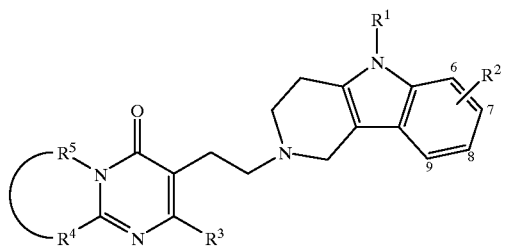

| Co. No. | Ex. No. | R¹ | R² | R³ | —R⁴—R⁵— | Physical data melting point in ° C. |
|---|---|---|---|---|---|---|
| 66 | B1b | 4-F-phenyl | 8-F | CH₃ | —CH₂—CH₂—CH₂—CH₂— | 174.6° C. |
| 67 | B1a | 4-F-phenyl | 8-F | CH₃ | —S—CH₂—CH₂— | 186.4° C. |
| 68 | B1a | 4-F-phenyl | 8-F | CH₃ | —S—CH=C(CH₃)— | 121.7° C. |
| 69 | B1c | benzyl | H | CH₃ | —CH=CH—CH=CH— | 156.6° C. |
| 70 | B1c | benzyl | H | CH₃ | —S—CH=CH— | 165.2° C. |
| 71 | B1c | benzyl | H | CH₃ | —CH₂—CH₂—CH₂—CH₂— | 132.2° C. |
| 72 | B1c | benzyl | H | CH₃ | —S—CH₂—CH₂— | 157.9° C. |
| 73 | B1c | benzyl | 8-OH | CH₃ | —CH=CH—CH=CH— | 158.8° C. |
| 74 | B1c | benzyl | 8-OH | CH₃ | —S—CH=CH— | 134.9° C. |
| 75 | B1c | benzyl | 8-OH | CH₃ | —CH₂—CH₂—CH₂—CH₂— | 130.3° C. |
| 76 | B1c | benzyl | 8-OH | CH₃ | —CH=CH—CH=CH— | 212.0° C. |
| 77 | B1c | benzyl | H | phenyl | —CH=CH—CH=CH— | 183.2° C. |
| 78 | B1c | benzyl | H | benzyl | —CH=CH—CH=CH— | 213.3° C.; fumaric acid |
| 79 | B1c | CH₃ | H | phenyl | —CH=CH—CH=CH— | 151.2° C. |
| 80 | B1c | CH₃ | H | benzyl | —CH=CH—CH=CH— | 151.8° C. |
| 81 | B1c | CH₃ | H | CH₃ | —CH₂—CH₂—CH₂—CH₂— | 157.7° C. |
| 82 | B1c | CH₃ | H | CH₃ | —CH=CH—CH=CH— | 117.6° C. |
| 83 | B1c | CH₃ | H | CH₃ | —S—CH₂—CH₂— | 182.4° C. |
| 84 | B1c | CH₃ | H | CH₃ | —S—CH=CH— | 152.9° C. |
| 85 | B1c | (CH₂)₃CH₃ | H | CH₃ | —S—CH₂—CH₂— | 158.8° C.; fumaric acid(2:1); H₂O |
| 86 | B1c | phenyl | H | CH₃ | —S—CH₂—CH₂— | 199.7° C. |
| 87 | B1c | phenyl | H | CH₃ | —S—CH=CH— | 172.5° C. |
| 88 | B1c | phenyl | H | CH₃ | —CH=CH—CH=CH— | 157.3° C. |
| 89 | B1c | phenyl | H | CH₃ | —CH₂—CH₂—CH₂—CH₂— | 163.8° C. |

TABLE 4

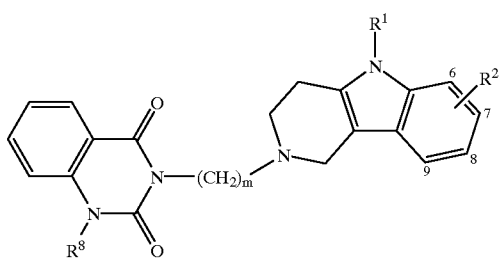

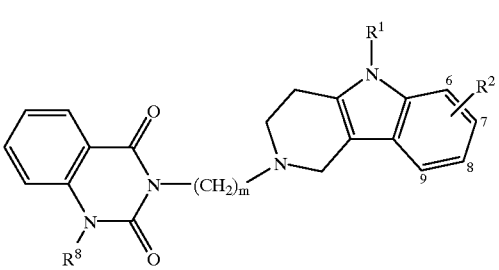

| Co. No. | Ex. No. | R¹ | R² | R⁸ | m | Physical data melting point in ° C. |
|---|---|---|---|---|---|---|
| 90 | B1a | H | 8-F | H | 2 | 227.2° C. |
| 91 | B1c | H | H | CH₃ | 2 | 240.0° C. |
| 92 | B1c | H | H | phenyl | 2 | 173.9° C. |
| 93 | B1c | benzyl | H | H | 2 | 201.9° C. |
| 94 | B1c | benzyl | H | H | 3 | 213.6° C. |
| 95 | B1c | phenyl | H | H | 2 | 208.9° C. |
| 121 | B1a | H | H | H | 4 | 239.4° C. |

TABLE 5

| Co. No. | Ex. No. | R¹ | R² | D-Alk- | Physical data melting point in ° C. |
|---|---|---|---|---|---|
| 96 | B1c | 4-F-phenyl | 8-F | benzothiazolo-pyrimidinone with 2-CH₃, 3-CH₂CH₂- | 196.1° C. |
| 97 | B1c | H | 8-F | benzothiazolo-pyrimidinone with 2-CH₃, 3-CH₂CH₂- | 255.6° C. |
| 98 | B1c | H | H | benzimidazolo-pyrimidinone with N-CH₃, 2-CH₃, 3-CH₂CH₂- | 240.0° C. |
| 99 | B1c | H | H | 1,3-dimethylxanthine-7-CH₂CH₂- | 215.5° C. |
| 117 | B1d | CH₃ | H | 4-F-phenyl-C(=O)-N(3-piperidinyl)-CH₂- | 202.5° C.; fumaric acid |
| 118 | B2 | CH₃ | H | 4-F-phenyl-C(=O)-N(4-piperidinyl)-CH₂- | 1480° C. |
| 119 | B2 | H | 8-F | 4-F-phenyl-C(=O)-N(3-piperidinyl)-CH₂- | 153.5° C. |

TABLE 5-continued

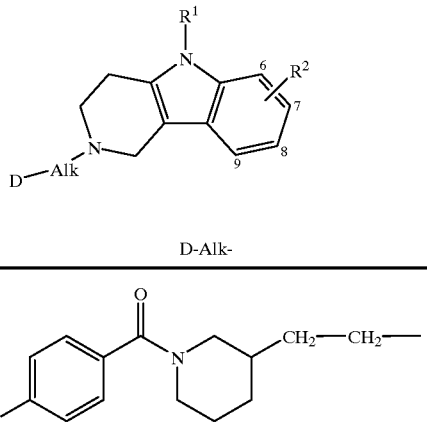

| Co. No. | Ex. No. | R¹ | R² | D-Alk- | Physical data melting point in ° C. |
|---|---|---|---|---|---|
| 120 | B1h | H | H | (4-F-C₆H₄-C(=O)-N-piperidin-3-yl)-CH₂-CH₂- | fumaric acid(2:3) |

TABLE 7

| Co. No. | Ex. No. | R⁴ | m | Physical data melting point in ° C. |
|---|---|---|---|---|
| 100 | B1c | NH₂ | 2 | 190.7° C.; H₂O(2:1) |
| 101 | B1c | NH₂ | 3 | 170.6° C. |
| 102 | B1c | NH(CH₃) | 2 | 139.9° C.; H₂O |
| 103 | B1c | NH(benzyl) | 2 | 199.9° C. |
| 104 | B1a | NH(CH₂CH₂CH₃) | 3 | 133.9° C. |

TABLE 8

| Co. No. | Ex. No. | R¹ | R² | X | m | Physical data melting point in ° C. |
|---|---|---|---|---|---|---|
| 105 | B.4 | CH₃ | H | NH | 3 | 257.1° C.; H₂O(2:1); HCl(1:2) |
| 106 | B3a | H | H | S | 3 | 211.1° C.; fumaric acid(2:1) |
| 107 | B3a | H | H | S | 4 | 179.8° C. |
| 108 | B3b | H | 8-F | S | 4 | 177.6° C. |
| 109 | B3b | H | 8-F | S | 3 | 164.8° C. |
| 110 | B3b | H | 8-OCH₃ | S | 4 | 187.5° C.; fumaric acid(1:2) |
| 111 | B3b | H | 8-OCH₃ | S | 3 | 193.7° C. |
| 112 | B3a | H | 8-CH₃ | S | 3 | 209.8° C.; HCl(1:2) |
| 113 | B3a | H | 8-CH₃ | S | 4 | 226.2° C.; HCl(1:2) |
| 114 | B3a | H | 8-Cl | S | 3 | 150.4° C. |
| 115 | B3b | H | 7-Cl | S | 3 | 228.6° C.; fumaric acid(2:3) |
| 116 | B3b | H | 7-Cl | S | 4 | 202.1° C.; fumaric acid |

C. Pharmacological Example

EXAMPLE C.1

5HT₂ receptors were measured by radioligand binding studies either in homogenates from rat brains or in a membranes fraction prepared from L929sA cells (mouse fibro carcinoma cells), stably transfected with human 5HT$_{2A}$ receptor cDNA.

Sample preparation

5HT₂ binding in rat frontal cortex

5HT₂ receptors were measured in a rat frontal cortex membrane fraction. Herefore wistar rats were killed by decapitation, brains were removed and frontal cortex was dissected. The frontal cortex was homogenized in Tris-HCL buffer 50 mM pH7.7. The homogenate was centrifuged at 23.000 g for 10 minutes. The resulting pellet was washed twice by resuspension and recentrifugation and the pellet was finally suspended in Tris-HCL buffer 50 mM pH7.7 in a dilution of 100 (vol/wet weight of tissue). 400 μl of the homogenate was incubated with 1 nM [³H]ketanserin in a total incubation volume of 0.5 ml for 30 minutes at 37° C. The incubation was stopped by rapid filtration using a manual filtration manifold. The filters were rinsed twice with ice-cold buffer and were counted in a liquid scintillation counter. Non-specific binding was determined in the presence of 1 μM methysergide.

5HT$_{2A}$ binding in L929sA cells

L929sA cells expressing human 5HT$_{2A}$ receptors were cultured in Petri dishes in DMEM medium(Gibco cat.nr. 41965–039) enriched with 5% heat inactivated fetal calf serum and in the presence of penicillin and streptomycin sulphate. 24 h before collection, cells were induced with m-interferon-b (1000 U/ml medium). Cells were collected by scrapping and centrifugation at low speed (5 minutes at 1500 g). The cells were homogenized and centrifuged for 10 minutes at 23.000 g. The resulting pellet was diluted in Tris-HCl 50 mM pH 7.7 and stored at −70° C. On the day of the experiment, a vial was thawed and diluted in Tris-HCl buffer. 5HT$_{2A}$ receptors are labeled with 0.1 nM [$^{125}$I] 4-amino-N-[1-[3-(4-fluorophenoxy)propyl]-4-methyl-4-piperidinyl ]-2-methoxybenzamide dihydrate. Membranes (0.2 ml) were incubated with the radioligand for 60 minutes at 37° C. in a total volume of 0.25 ml. The reaction was stopped by rapid filtration and the filter rounds were counted in an auto-gamma spectrophotometer.

Data analysis

Counting data from assays in the presence of test compound were automatically expressed as percent of total binding measured in the absence of test compound. Therefrom, the pIC$_{50}$ (-log IC$_{50}$)-values (IC$_{50}$= concentration in M inhibiting 50% of the specific radioligand binding or neurotransmitter uptake) were derived and are listed in Table 9 (a "–" means "not measured").

TABLE 9

| Comp. No. | 5HT$_2$-binding | 5HT$_{2A}$-binding |
| --- | --- | --- |
| 1 | 8.41 | 7.88 |
| 2 | 7.44 | — |
| 4 | 7.9 | — |
| 5 | — | 8.51 |
| 6 | 9 | 8.19 |
| 7 | 8.12 | 7.64 |
| 8 | 8.37 | 8.01 |
| 9 | 8.02 | 7.24 |
| 10 | 7.59 | 6.34 |
| 11 | — | 6.24 |
| 12 | — | 6.21 |
| 13 | — | 5.83 |
| 14 | — | 6.38 |
| 15 | — | 5 |
| 16 | — | 6.9 |
| 17 | — | 6.6 |
| 18 | — | 5.6 |
| 20 | — | 6.5 |
| 21 | — | 7 |
| 22 | — | 6.2 |
| 23 | 9 | 8.63 |
| 24 | 8.71 | 8.07 |
| 25 | — | 8.48 |
| 26 | — | 8.21 |
| 27 | 8.55 | — |
| 28 | 8.91 | 8.12 |
| 30 | 8.79 | 8.08 |
| 32 | 9.4 | 8.35 |
| 33 | 8.35 | — |
| 35 | 8.43 | — |
| 36 | — | 6.5 |
| 37 | 8.49 | 7.35 |
| 38 | 8.09 | 7.9 |
| 39 | 8.58 | 8.3 |
| 41 | 7.84 | — |
| 52 | 7.54 | 7.31 |
| 53 | 7.75 | 7.63 |
| 67 | 8.74 | 8.36 |
| 68 | — | 8.18 |
| 69 | 7.95 | — |
| 86 | — | 8.34 |
| 89 | — | 8.16 |
| 100 | 8.3 | — |

TABLE 9-continued

| Comp. No. | 5HT$_2$-binding | 5HT$_{2A}$-binding |
| --- | --- | --- |
| 108 | 6.26 | — |
| 116 | 5.85 | — |

EXAMPLE C.2

In vitro binding affinity for $\alpha_2$ receptors The interaction of the compounds of formula (I) with $\alpha_2$ receptors was assessed in a in vitro radioligand binding experiment.

In general, a low concentration of a radioligand with a high binding affinity for a particular receptor is incubated with a sample of a tissue preparation enriched in a particular receptor or with a preparation of cells expressing cloned human receptors in a buffered medium. During the incubation, the radioligand binds to the receptor. When equilibrium of binding is reached, the receptor bound radioactivity is separated from the non-bound radioactivity, and the receptor bound activity is counted. The interaction of the test compounds with the receptor is assessed in competition binding experiments. Various concentrations of the test compound are added to the incubation mixture containing the receptor preparation and the radioligand. Binding of the radioligand will be inhibited by the test compound in proportion to its binding affinity and its concentration.

The radioligand used for $\alpha_2$ receptor binding was $^3$H-clonidine and the tissue preparation used was the cortex of the rat. The compounds with number 1 to 11, 13, 14, 16, 17, 20, 23 to 41, 43, 52 to 57, 60, 63, 66 to 74, 81 to 89 and 96 to 98 produced an inhibition of more than 50% at a test concentration of 10$^{-6}$ M or less, and the other compounds produced an inhibition of less than 50% at a test concentration of 10$^{-6}$ M.

D. Composition examples

"Active ingredient" (A.I.) as used throughout these examples relates to a compound of formula (I), a pharmaceutically acceptable addition salt or a stereochemically isomeric form thereof.

EXAMPLE D.1: Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE D.2

Film-coated tablets

Preparation of tablet core

A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3- propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

EXAMPLE D.3

Oral solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE D.4

Injectable solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

What is claimed is:
1. A compound of formula:

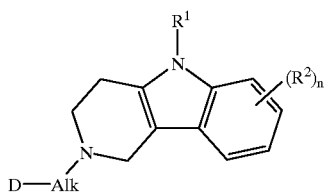

(I)

a N-oxide form, a pharmaceutically acceptable addition salt or a stereochemically isomeric form thereof, wherein:

$R^1$ is hydrogen, $C_{1-6}$alkyl, aryl or $C_{1-6}$alkyl substituted with aryl;
$R^2$ is each independently a halogen, hydroxy, $C_{1-6}$alkyl, $C_{1-6}$alkyloxy or nitro;
n is 0, 1, 2 or 3;
Alk is $C_{1-6}$alkanediyl;

D is a radical of formula

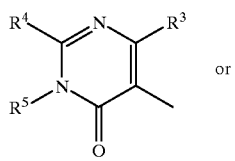

(a)

or

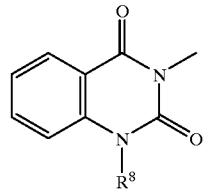

(c)

wherein
each
$R^3$ is hydrogen, $C_{1-6}$alkyl, aryl or aryl$C_{1-6}$alkyl;
$R^4$ is hydrogen, $C_{1-6}$alkyl, $C_{1-6}$alkyloxy, $C_{1-6}$alkylthio, amino, mono- or di ($C_{1-6}$alkyl)amino or mono- or di(aryl$C_{1-6}$alkyl)amino;
$R^5$ is hydrogen or $C_{1-6}$alkyl;
$R^8$ is hydrogen, $C_{1-6}$alkyl or aryl; or
$R^4$ and $R^5$ taken together may form a bivalent radical —$R^4$—$R^5$— of formula

| | |
|---|---|
| —CH$_2$—CH$_2$—CH$_2$— | (a-1); |
| —CH$_2$—CH$_2$—CH$_2$—CH$_2$— | (a-2); |
| —CH=CH—CH$_2$— | (a-3); |
| —CH$_2$—CH=CH— | (a-4) or |
| —CH=CH—CH=CH— | (a-5); | wherein one or two hydrogen atoms of said radicals (a-1) to (a-5) each independently may be replaced by halogen, $C_{1-6}$lkyl, aryl$C_{1-6}$alkyl, trifluoromethyl, amino, hydroxy, $C_{1-6}$alkyloxy or $C_{1-10}$alkylcarbonyloxy;
or where possible, two geminal hydrogen atoms may be replaced by $C_{1-6}$alkylidene or aryl$C_{1-6}$alkylidene; or
—$R^4$—$R^5$— may also be

| | |
|---|---|
| —S—CH$_2$—CH$_2$— | (a-6) |
| —S—CH$_2$—CH$_2$—CH$_2$— | (a-7); |
| —S—CH=CH— | (a-8); |
| —NH—CH$_2$—CH$_2$— | (a-9); |
| —NH—CH$_2$—CH$_2$—CH$_2$— | (a-10); |
| —NH—CH=CH— | (a-11); |
| —NH—CH=N— | (a-12); |
| —S—CH=N— | (a-13) or |
| —CH=CH—O— | (a-14); | wherein one or where possible two or three hydrogen atoms in said radicals (a-6) to (a-14) each independently may be replaced by $C_{1-4}$alkyl or aryl; and aryl is phenyl or phenyl substituted with a halogen or $C_{1-6}$alkyl.

2. A compound according to claim 1 wherein n is 0 or 1 and $R^2$ is positioned in the 6-, 7- or 8-position of the γ-carboline moiety.

3. A compound according to claim 2 wherein $R^2$ is halogen, hydroxy, $C_{1-6}$alkyl or $C_{1-6}$alkyloxy; n is 0 or 1, Alk is $C_{1-4}$alkanediyl; D is a radical of formula (a) wherein $R^3$ is $C_{1-6}$alkyl, $R^4$ is amino, or —$R^4$—$R^5$— is a radical of formula (a-2) or (a-5) wherein one or two hydrogen atoms each independently may be replaced by halogen, $C_{1-6}$alkyl, trifluoromethyl or $C_{1-6}$alkyloxy, or —$R^4$—$R^5$— is a radical of formula (a-6), (a7), (a-8), (a-11), (a-13) or (a-14) wherein one or where possible two hydrogen atoms each independently may be replaced by $C_{1-6}$alkyl.

4. A compound according to claim 1 wherein $R^1$ is hydrogen; n is 0 or n is 1 whereby $R^2$ is a halogen, $C_{1-6}$alkyl, or $C_{1-6}$alkoxy; Alk is 1,2-ethanediyl and D is a radical of formula (a) wherein $R^3$ is $C_{1-6}$alkyl, $R^4$ is amino, $R^5$ is $C_{1-6}$alkyl, or —$R^4$—$R^5$— is a radical of formula (a-2), (a-5), (a-6), (a-7), (a-8) or (a-11) wherein one hydrogen atom may be replaced by $C_{1-6}$alkyl.

5. A compound according to claim 1 wherein $R^1$ is hydrogen; n is 0 or n is 1 whereby $R^2$ is a halogen or $C_{1-6}$alkyl; Alk is 1,2-ethanediyl and D is a radical of formula (a) wherein $R^3$ is $C_{1-6}$alkyl, $R^4$ and $R^5$ are taken together to form —$R^4$—$R^5$— of formula (a-2), (a-5), (a-6), (a-7) or (a-8) wherein one hydrogen atom may be replaced by $C_{1-6}$alkyl.

6. A compound according to claim 1 wherein $R^1$ is hydrogen, methyl, n-butyl, phenyl, benzyl or 4-fluorophenyl.

7. A composition comprising a pharmaceutically acceptable carrier and, as active ingredient, a therapeutically effective amount of a compound as claimed in claim 1.

8. A process for preparing a pharmaceutical composition comprising combining a compound of claim 1 as the active ingredient in intimate admixture with a pharmaceutically acceptable carrier.

9. A process for preparing a compound according to claim 1, characterized by, a) N-alkylating a 1,3,4,5-tetrahydro-2H-pyrido[4,3-b] indole derivative of formula (II) with an alkylating reagent of formula (III)

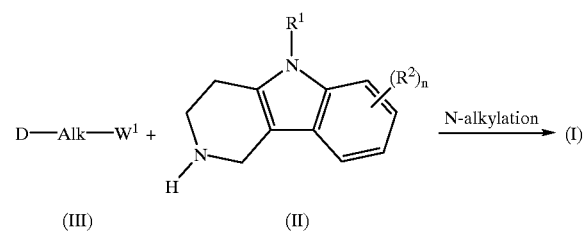

wherein $W^1$ represents an appropriate reactive leaving group and D, Alk, n, $R^1$ and $R^2$ are as defined in claim 1, in a reaction-inert solvent and in the presence of a suitable base and optionally in the presence of a catalyst;

b) and if desired, converting the compounds of formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, if desired, preparing stereochemically isomeric forms or N-oxides thereof.

10. A method of treating a psychotic disorder in a warm-blooded animal in need thereof comprising administering to the warm-blooded animal a therapeutically effective amount of the compound of claim 1.

11. The method of claim 10 wherein the psychotic disorder is selected from depression, anxiety or psychosis.

* * * * *

UNITED STATES PATENT AND TRADEMARK OFFICE
CERTIFICATE OF CORRECTION

PATENT NO. : 6,303,614 B1 Page 1 of 1
DATED : October 16, 2001
INVENTOR(S) : Ludo Edmond Josephine Kennis and Josephus Carolus Mertens It is certified that error appears in the above-identified patent and that said Letters Patent is hereby corrected as shown below:

Column 30,
Line 41, replace "$C_{1-6}$lkyl" with -- $C_{1-6}$alkyl --
Line 65, replace "$C_{1-4}$alkyl" with -- $C_{1-6}$alkyl --

Column 31,
Line 11, replace "(a7)" with -- (a-7) --

Signed and Sealed this

Fourth Day of November, 2003

JAMES E. ROGAN
*Director of the United States Patent and Trademark Office*